United States Patent
Rada

(10) Patent No.: US 9,801,991 B2
(45) Date of Patent: Oct. 31, 2017

(54) DISPOSABLE CASSETTE WITH LUER LOCKS AND METHOD FOR PACKAGING

(71) Applicant: GAMBRO LUNDIA AB, Lund (SE)

(72) Inventor: Hiram Rada, Lyons (FR)

(73) Assignee: Gambro Lundia AB, Lund (SE)

( * ) Notice: Subject to any disclaimer, the term of this patent is extended or adjusted under 35 U.S.C. 154(b) by 297 days.

(21) Appl. No.: 14/652,936

(22) PCT Filed: Dec. 18, 2013

(86) PCT No.: PCT/IB2013/061086
§ 371 (c)(1),
(2) Date: Jun. 17, 2015

(87) PCT Pub. No.: WO2014/097175
PCT Pub. Date: Jun. 26, 2014

(65) Prior Publication Data
US 2015/0335806 A1   Nov. 26, 2015

Related U.S. Application Data

(60) Provisional application No. 61/739,196, filed on Dec. 19, 2012.

(30) Foreign Application Priority Data

Dec. 19, 2012   (EP) .................................... 12197954

(51) Int. Cl.
*A61M 1/16* (2006.01)
*A61M 1/14* (2006.01)
(Continued)

(52) U.S. Cl.
CPC .............. *A61M 1/14* (2013.01); *A61M 1/169* (2013.01); *A61M 5/002* (2013.01);
(Continued)

(58) Field of Classification Search
CPC ................ A61M 2205/12; A61M 1/14; A61M 2039/1033; A61M 5/002; A61M 2209/06; A61M 2209/08
See application file for complete search history.

(56) References Cited

U.S. PATENT DOCUMENTS 6,071,269 A    6/2000  Schnell et al.
2003/0159966 A1* 8/2003 McMichael ............ A61B 50/30
                                                  206/570

(Continued)

FOREIGN PATENT DOCUMENTS

EP        1066853       1/2001
WO     2011008624       1/2011

OTHER PUBLICATIONS

International Search Report—PCT/IB2013/061086—dated Mar. 11, 2014—3 pages.
(Continued)

*Primary Examiner* — Leslie Deak
(74) *Attorney, Agent, or Firm* — K&L Gates LLP

(57) ABSTRACT

An extracorporeal circuit has been conceived including: lines (16) which include passages for blood or a medical liquid; a connector (38, 40) at a free end of each of the lines (16); a cassette (18) supporting the lines, and dummy connectors (42, 44) attached to the cassette (18) and each adapted to form a mating connection with a respective one of the connectors (38, 40) at the free ends of the lines (16), wherein the connectors (38, 40) are arranged in accordance with a sequence in which the lines (16) are attached for a blood treatment session or are grouped in accordance with types of liquids to flow through the lines (16) during the blood treatment session. The extracorporeal circuit may be a circuit for dialysis and the circuit includes a hemodialyzer. Further, the connectors (38, 40) and dummy connectors (42,
(Continued)

44) may each be one of a male or female luer lock connector, and the dummy connectors (42, 44) may include both male and female connectors.

33 Claims, 2 Drawing Sheets

(51) Int. Cl.
  *A61M 5/00* (2006.01)
  *A61M 39/10* (2006.01)
(52) U.S. Cl.
  CPC . *A61M 2039/1033* (2013.01); *A61M 2205/12* (2013.01); *A61M 2209/06* (2013.01); *A61M 2209/08* (2013.01)

(56) References Cited

U.S. PATENT DOCUMENTS

2003/0217976 A1\* 11/2003 Bowman, Jr. ........... A61M 1/28
  210/739
2009/0012448 A1\* 1/2009 Childers ................. A61M 1/14
  604/29

OTHER PUBLICATIONS

Written Opinion—PCT/IB2013/061086—dated Mar. 11, 2014—9 pages.
EP Search Report—EP Appl. No. 12197954.6-1651—dated May 15, 2013—11 pages.

\* cited by examiner

DISPOSABLE CASSETTE WITH LUER LOCKS AND METHOD FOR PACKAGING

CROSS-REFERENCE TO RELATED APPLICATIONS

The present application is a National Phase of International Application No. PCT/IB2013/061086, filed on Dec. 18, 2013, which claims priority to European Patent Application No. 12197954.6, filed Dec. 19, 2012, and U.S. Provisional Application No. 61/739,196, filed Dec. 19, 2012, the entire contents of each of which is incorporated herein by reference and relied upon.

BACKGROUND OF THE INVENTION

The field of the invention relates generally to extracorporeal circuits for extracorporeal treatment. The field relates specifically to stowing the flexible lines of an extracorporeal circuit prior to and after use of the circuit in a blood treatment therapy and packaging extracorporeal circuits prior to their use.

Blood treatment systems, such as used for dialysis or ultrafiltration treatments, typically include disposable extracorporeal circuit and an extracoporeal treatment monitor on which the extracorporeal circuit is mounted. The extracorporeal circuit includes flexible lines providing passages for blood, blood treatment fluids, dialysate and other liquids. The lines connect, for example, to a vascular access device associated with a patient, sources of priming and treatment fluids, containers to receive dialysate and other liquids discharged from the extracorporeal circuit and other devices used for treating blood.

Several of the lines of a disposable extracorporeal circuit have free ends with connectors. These free ends connect to the vascular access device of a patient, sources of liquids and containers in or on the monitor, and the other devices associated with treating blood. The connections of the free ends of the lines are typically made after the extracorporeal circuit is mounted to the monitor and the patient is ready for blood treatment therapy. Until these connections are made, the free ends are capped to ensure that the passages in the lines remain sterile and undamaged.

The caps on most conventional extracorporeal circuits are small individual components. A cap may be a plastic luer lock cap that entirely separates from the extracorporeal circuit once removed from the free end of a line. After being removed from the ends of the lines, the caps tend to be lost or discarded. When lost or discarded, the caps are not available to recap the line after the blood treatment therapy and when the extracorporeal circuit is ready to be disposed.

As an alternative to a cap, a dummy luer lock connection in the housing of a bubble trap chamber is disclosed in U.S. Pat. No. 6,071,269. The dummy luer lock is a connector for a free end of a line in an extracorporeal circuit where the connector is used solely to hold the end of a line when not in use.

The free ends of lines tend to be associated with relatively lengthy sections of the lines that reach from the extracorporeal circuit to the vascular access device, source of blood or liquid or container. Specifically, the free ends are on lines that tend to be thin, plastic tubes which may have lengths of a meter or more. Extracorporeal circuits tend to have several lines, such as six or more. The lines with free ends tend to become disordered and tangled before they are connected for a blood treatment therapy. Keeping the lines untangled and ordered is an ongoing problem of extracorporeal circuits. There is a long felt need for devices and techniques to securely cap the free ends of lines of an extracorporeal circuit and stow the free ends in an orderly manner.

In addition to a need for organizing and stowing the lines of a disposable extracorporeal circuit, there is a long felt need to enhance the sterilization of a disposable extracorporeal circuit. Aseptic packaging systems inject ethylene oxide (EtO) into packaging for medical devices to sterilize the device. Ansari and Datta, AN OVERVIEW OF STERILIZATION METHODS FOR PACKAGING MATERIALS USED IN ASEPTIC PACKAGING SYSTEMS, Trans IChemE, Vol. 81, Part C, pp. 57-65 (2003). It can be difficult for the EtO injected into packaging to reach the interior passages of the lines of the extracorporeal circuit. There is a long-felt need to enhance the delivery of EtO into packaging for disposable extracorporeal circuits and, particularly, to the passages of the lines.

BRIEF SUMMARY

The invention provides a convenient means to stow and organize the free ends of lines, e.g., tubes, for blood and other fluid in an extracorporeal circuit and to sterilize the circuit when in packaging. Dummy luer connectors are arranged on a cassette for the circuit to hold the free ends of the lines until the lines are to be used for a treatment. The dummy luer connectors are arranged on the cassette in a manner that groups the lines such that they are conveniently organized for connection to the patient, sources of liquids and containers to receive liquid.

The dummy luer connectors and their arrangement on the cassette provide an ease of use advantage, among other advantages, to the extracorporeal circuit. The dummy luer lock connectors are arranged in a manner corresponding to or suggestive of the proper connections to be made between the free ends of lines and the vascular access device, sources of or containers for liquids or other connections. By way of example, the dummy luer lock connectors may be arranged around the perimeter of a cassette corresponding to the sequence in which the free ends of lines are to be connected or grouped on the cassette by the function of the free ends.

The invention also arranges hydrophobic filters on the extracorporeal circuit and its packaging to enhance sterilization of the extracorporeal circuit. In particular, hydrophobic filters may be included in certain components, e.g., the lines, of an extracorporeal circuit. The hydrophobic filter panels allow sterilization gas injected into the packaging of an extracorporeal circuit to flow into the passages of the lines of the circuit. Hydrophobic filter panels may be included in the packaging and aligned with the hydrophobic filters on the lines.

An extracorporeal circuit has been conceived comprising: lines which include passages for blood or a medical liquid; a connector at a free end of each of the lines; a cassette supporting the lines, and dummy connectors attached to the cassette and each adapted to form a mating connection with a respective one of the connectors at the free ends of the lines, wherein the connectors are arranged in accordance with a sequence in which the lines are attached for a blood treatment session or are grouped in accordance with types of liquids to flow through the lines during the blood treatment session. The extracorporeal circuit may be a circuit for dialysis and the circuit includes a hemodialyzer. Further, the connectors and dummy connectors may each be one of a male or female luer lock connector, and the dummy connectors may include both male and female connectors.

In an aspect, the dummy connectors are arranged in a plurality of groups, wherein each group corresponds to a step of a sequence in which the lines are attached for a blood treatment session.

In an aspect, the dummy connectors are arranged in a plurality of groups, wherein each group corresponds to types of liquids to flow through the lines.

In an aspect, the groups of dummy connectors are located on different zones of the cassette.

In an aspect, the cassette comprises a front wall and sidewalls and a first group of the dummy connectors is attached to one of the walls of the cassette and a second group of the dummy connectors is attached to another wall of the cassette.

In an aspect, the lines associated with preparation of the extracorporeal circuit are connected to the dummy connectors on a first side of the cassette, the lines associated with blood and anti-coagulant are connected to the dummy connectors on a second side of the cassette, the lines associated with blood treatment fluid and dialysate are connected to the dummy connectors on a third side of the cassette.

In an aspect, the extracorporeal circuit comprises mounting brackets attached to the cassette, wherein the dummy connectors extend from the mounting brackets.

In an aspect, the mounting brackets are releasably attached to the cassette.

In an aspect, the mounting brackets are permanently attached to the cassette.

The dummy connectors may protrude from a first bracket and a second bracket each attached to the cassette, wherein the first bracket has dummy connectors to connect to the lines for blood, and the second bracket having dummy connectors to connect to the lines for a blood treatment liquid and a dialysate. The dummy connectors may be arranged in a first group of the dummy connectors are attached to a sidewall of the cassette and a second group of the dummy connectors are attached to a front wall of the cassette. Further, a first group of the dummy connectors protrude in an orthogonal direction to a direction of protrusion of a second group of the dummy connectors.

The dummy connectors may include: a first group of the dummy connectors designated to stow the lines associated with moving a replacement fluid into the circuit and discharging replacement fluid effluent from the circuit or may be lines associated with moving anticoagulant, e.g., citrate, into and out of the circuit; a second group of the dummy connectors designated to stow the lines associated with blood access to a vascular system of a patient, and a third group of the dummy connectors designated to stow the lines associated with moving a blood treatment fluid, e.g., dialysate, into the circuit and discharging dialysate effluent from the circuit or moving a replacement fluid into and out of the circuit.

An extracorporeal circuit has been conceived comprising: flexible medical tubing lines providing passages for blood or a medical liquid to flow through the circuit; luer lock connectors each capping a free end of one of the tubing lines, wherein each of the luer lock connectors includes a liquid passage continuous to the passage in the tubing line capped by the luer lock connector; at least one cassette supporting the tubing lines and configured to mount to a extracorporeal treatment monitor including pumps adapted to engage the tubing lines to move liquids through the lines of the circuit, and dummy luer connectors attached to the cassette and each configured to form a mating connection to one of the luer lock connectors capping the free end of one of the tubing lines, wherein the dummy luer lock connectors each seal closed the free end of the passage of the tubing lines connected to the dummy luer lock connector, wherein the dummy luer lock connectors are configured to stow the free ends of the tubing lines to the cassette, and are arranged in accordance with a sequence in which the tubing lines are attached for a blood treatment session or are grouped in accordance with types of liquids to flow through the tubing lines.

A method has been conceived to stow free ends of lines in an extracorporeal circuit including a cassette and lines having passages for liquids, the method comprising: attaching a connector to cap a free end of one of the lines, wherein the connector includes a passage aligned with the passage of the capped line; assigning each of a plurality of dummy connectors to a respective one of the capped free ends of the lines; arranging the dummy connectors in groups and positioning the groups of dummy connectors on the cassette, wherein the groups correspond to a sequence in which the lines are to be attached for a blood treatment session or correspond to types of liquids to flow through the lines while the circuit is in use; stowing the free ends by coupling the connectors capping the free end of the lines to a respective one of the dummy connectors, and packaging the circuit with the stowed free ends of the lines in a package for shipment of the circuit.

In an aspect, the connectors and the dummy connectors are each one of a male or female luer lock connector.

In an aspect, each group corresponds to a step of a sequence in which the lines are attached for a blood treatment session.

In an aspect, each group corresponds to types of liquids to flow through the lines.

In an aspect, the groups of dummy connectors are positioned on different zones of the cassette.

In an aspect, the cassette comprises a front wall and sidewalls and wherein a first group of the dummy connectors is positioned on one of the walls of the cassette and a second group of the dummy connectors is positioned on another wall of the cassette.

An extracorporeal circuit has been conceived comprising: flexible medical tubing lines providing passages for blood or a medical liquid to flow through the circuit; luer lock connectors each capping a free end of one of the tubing lines, wherein each of the luer lock connectors includes a liquid passage continuous to the passage in the tubing line capped by the luer lock connector; at least one cassette supporting the tubing lines and configured to mount to a extracorporeal treatment monitor including pumps adapted to engage the tubing lines to move liquids through the lines of the circuit; dummy luer connectors attached to the cassette and each configured to form a mating connection to one of the luer lock connectors capping the free end of one of the tubing lines, wherein the dummy luer lock connectors each seal closed the free end of the passage of the tubing lines connected to the dummy luer lock connector, and a hydrophobic filter connected to at least one of the tubing lines having one of the free ends capped with the luer lock connector, wherein the hydrophobic filter is permeable to gas and impermeable to liquids. The hydrophobic filter may be a segment of the at least one of the tubing lines. Each of the tubing lines having a free end capped with the luer lock connector may include a hydrophobic filter.

A package for an extracorporeal circuit has been conceived comprising an envelope; an extracorporeal circuit comprising lines and a cassette supporting the lines; a connector at the free end of each line; dummy connectors attached to the cassette and each coupled with a respective one of the connectors at the free ends of the lines, wherein the dummy connectors are arranged in groups and positioned on the cassette wherein the groups correspond to a sequence in which the lines are to be attached for a blood treatment session or correspond to types of liquids to flow through the lines; wherein the cassette comprises a front wall and sidewalls; wherein a first group of the dummy connectors is attached to one of the walls of the cassette and a second group of the dummy connectors is attached to another wall of the cassette; wherein the extracorporeal circuit and the cassette are packaged in the envelope.

In an aspect, the lines associated with preparation of the extracorporeal circuit are connected to the dummy connectors on a first side of the cassette, lines associated with blood and anti-coagulant are connected to the dummy on a second side of the cassette, lines associated with blood treatment fluid and dialysate are connected to the dummy connectors on a third side of the cassette.

In an aspect, the extracorporeal circuit is for hemodialysis and the circuit includes a hemodialyzer.

In an aspect, the package comprises a hydrophobic filter connected to at least one of the lines.

In an aspect, the envelope includes at least one hydrophobic filter panel.

In an aspect, the envelope comprises opposing sheets sealed along a perimeter of the sheets and the hydrophobic filter panel is co-extensive with an opening in one of the sheets.

A package for an extracorporeal circuit has been conceived comprising an envelope including at least one hydrophobic filter panel providing a vent for a sterilization gas and a barrier to moisture and bacteria. A hydrophobic filter panel is connected, e.g., incorporated into, some or all of of the lines of the extracorporeal circuit. The filter panels in the lines allow sterilization gas to enter the lines and block liquids from leaking out of the lines.

The extracorporeal circuit may be for hemodialysis and include a hemodialyzer. The package may include opposing sheets sealed along a perimeter of the sheets, and the hydrophobic filter panel is co-extensive with an opening in one of the sheets.

DETAILED DESCRIPTION

Figure 1:
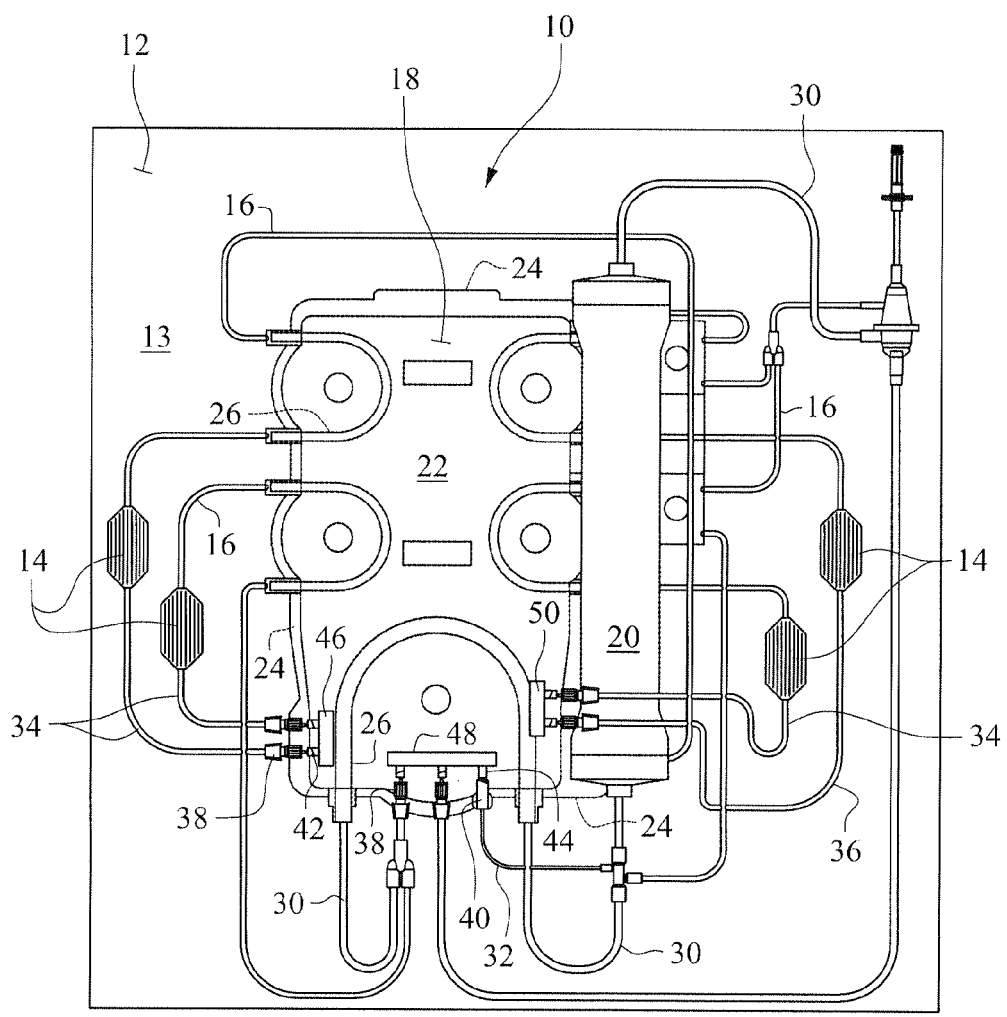
FIG. 1 is a schematic diagram of an extracorporeal circuit with tubing having luer locks, a cassette with dummy luer locks to stow loose ends of tubing, and hydrophobic membranes on the sheet(s) of packaging that provide an aseptic environment for the extracorporeal circuit prior to being mounted on a blood treatment monitor.

FIG. 1 is a front view of an exemplary extracorporeal circuit 10 sealed in a packaging envelope 12. The packaging envelope may be flexible, transparent plastic sheets 13 sealed along the edges of the sheets. The envelope is sufficiently large to contain the extracorporeal circuit 10 and optional packaging for the extracorporeal circuit, such as support panels for the circuit, its lines and other components.

Hydrophobic filters 14 are incorporated into one or more of the lines of the blood circuit. The filters may form a segment of a line as shown in FIG. 1, be at the end of a line, or incorporated in a dummy luer lock connecter to which a line is attached. The filters may be, for example, a sleeve that fit over the lines and are aligned with an opening in the lines, or a filter panel having an internal passage and forming a segment of a line. The filters allow sterilization gas to enter the passage in the line and ensure that the passage is sterilized. The filters may remain in place while liquids flow through the circuit because the panels are impervious to liquids.

Hydrophobic filter panels (not shown) are also incorporated into the sheets 13 provide vents allowing Ethylene Oxide (EtO) sterilization gas to exhaust from envelope. Filter panels in the sheets of an envelope are conventional. The hydrophobic filter panels include membranes that allow the EtO gas to enter and leave the envelope, while preventing moisture and bacteria from entering the envelope. The EtO gases kill bacteria in the envelope and on the extracorporeal circuit within the envelope. The filter panels may be arranged in the sheets to align with specific components of the extracorporeal circuit, such as the filters 14 in the lines. The arrangement of the filter panels in the sheet(s) of the envelope may be selected to ensure that the EtO sterilization gas is distributed through the envelope 12 and over all surfaces of the extracorporeal circuit. The arrangement of filter panels may also be arranged such that the panels do not abut the hard surfaces or edges of the extracorporeal circuit such as on the cassette 18 or the blood treatment device 20.

The disposable extracorporeal circuit 10 includes lines 16, such as medical grade, flexible plastic tubes. The lines provide passages for blood, blood treatment liquids and other liquids flowing through the extracorporeal circuit. The lines are connected to or mounted on the cassette 18 which is part of the extracorporeal circuit. The cassette 18 may be formed of a rigid plastic material and include molded components that fit together such as a back plate and a front plate 22. Sidewalls 24 at the perimeter of the cassette may extend between the back and front plates. The sidewalls 24 may be integral with the back or front plate.

The cassette 18 supports the lines 16 of the extracorporeal circuit. For example, the cassette may include mounts supporting semi-circular loops 26 for the lines 16. These loops 26 connect to pumps in a blood treatment monitor (see FIG. 2). The pumps, e.g., peristaltic pumps, mechanically act on the loops to move liquid through the lines at flow rates controlled by the pumps. The loops may be integral with the lines and be supported by supporting brackets on the cassette.

A blood treatment device 20, such as a hemodialyzer, may be attached to the cassette. Alternatively, the blood treatment device may be separate from the cassette. The blood treatment device is typically mounted to the blood treatment monitor when the cassette is mounted to the monitor. The lines 16 of the extracoporeal circuit attach to inlet and outlet ports of the blood treatment device. For example, lines may be blood lines 30 that carry withdrawn blood to be treated to the extracorporeal circuit or treated blood to be infused into the patient.

The flexible lines 16 typically have lengths corresponding to their function. For example, the blood lines 30 that carry blood to and from the patient have lengths sufficient to reach from the console to the patient. Similarly, a narrow, short line 32 connects a source of anti-coagulant, e.g., a replaceable bag or other container, to the extracorporeal circuit. Further, flexible lines 34 may connect the extracorporeal circuit to sources of other fluids, such as a priming solution or a blood treatment fluid. In addition, the lines 36 may connect to other containers for dialysate or other filtrate discharged from the blood treatment device 20.

The ends of the lines 30, 32, 34 and 36 are capped with connectors, such as a male luer lock connector 38 or female luer lock connector 40. These connectors are configured to form a connection with a blood access device, source of a liquid or a container to receive liquids. The connection forms a passage through which liquid flows into or out of the lines 30, 32, 34 and 36.

The ends of the lines 30, 32, 34 and 36 are connected to male or female dummy luer lock connectors 42, 44. A dummy luer lock connector is a mating connector fixed to an outer surface of the cassette. The dummy luer lock connector typically has a closed end and does not form a liquid passage into the cassette. The term "dummy" indicates that the luer lock connector is not used to connect fluid passages.

The dummy luer lock connectors provide connections for the free ends of lines while the extracorporeal circuit is in the envelope and while the lines are not connected to the patient, sources or receptacles of liquids or other devices associated with blood therapy. The dummy luer lock connector 42, 44 may not form an internal passage as do conventional luer lock connectors and may plugged to form a sealing cap for the free end of the lines. Male dummy luer lock connectors 44 provide a mating connection for female luer lock connectors 40 on the free ends of lines of the extracorporeal circuit. Similarly, female dummy luer lock connectors 42 provide a mating connection for male luer lock connectors 38 on the free ends of lines.

A dummy luer lock connector caps the ends of lines to stow the line and prevent the lines from becoming tangled with other lines of the circuit. A dummy luer lock connector may also prevent liquid from draining from the line to the floor after a circuit has been used in a blood therapy session.

The free ends of the lines are connected to the dummy luer lock connectors prior to the extracorporeal circuit being sealed in the envelope. The lines remain connected to the dummy luer lock connectors until the extracorporeal circuit is removed from the envelope and the cassette is connected to the monitor. A person, such as a nurse or health care technician, disconnects the luer lock connectors on free ends of the lines from the dummy luer locks and connects the luer lock free ends to the corresponding luer connectors on the sources of liquid, containers to receive liquids and other connectors intended to receive the free ends.

The dummy luer lock connectors 42, 44 may be permanently fixed or releasably mounted to the cassette. For example, the dummy luer lock connectors may extend from mounting brackets 46, 48 and 50 that are permanently or releasably attached to the front 22 or a sidewall 24 of the cassette 18.

In one embodiment, each bracket has dummy luer locks for a particular type of lines. A first bracket 46 has two dummy female luer lock connectors 42 to receive the free ends of lines for moving a replacement liquid into the circuit and discharge the effluent replacement fluid from the circuit. The circuit may be designed such that the dummy luer lock connectors of the first bracket receive the free ends of lines to move the anticoagulant, e.g., citrate, into the circuit. A second bracket 48 has three luer lock connectors (two female and one male) for the blood access lines and an anticoagulant line. The second bracket may group together the free ends of just the blood access lines or the blood access lines and the line coupled to a source of anticoagulant. A third bracket 50 has two female luer lock connectors for the dialysate and replacement fluid. The third bracket may group together the lines for moving dialysate or a blood treatment liquid through the extracorporeal circuit from a source of the liquid to a container receiving the liquid after passing through the circuit.

The dummy luer lock connectors are arranged on a cassette in an organized manner on the cassette. For example, the lines associated with preparation of the extracorporeal circuit, e.g., the lines for priming fluids, may connect to dummy luer lock connectors (see bracket 46) on a first side, e.g., the left sidewall, of the cassette. The dummy luer lock connectors (see bracket 48) lines for blood and anti-coagulant may be on a second side, e.g., the font 22, of the cassette. The dummy luer lock connectors (see bracket 50) associated with the blood treatment fluid and dialysate may be on a third side, e.g., the right sidewall, of the cassette.

The dummy luer lock connectors and their associated (optional) brackets may be arranged in various manners on the cassette. The arrangement of dummy luer lock connectors may be selected to achieve a desired organization. For example, the dummy luer lock connectors may be arranged such that the lines are stowed in a order corresponding to the sequence in which the lines are to be removed from the dummy luer lock connectors and connected to the active luer lock connectors. Alternatively, the dummy luer lock connectors may be arranged based on their function, such as is shown in FIG. 1 and described above.

Figure 2:
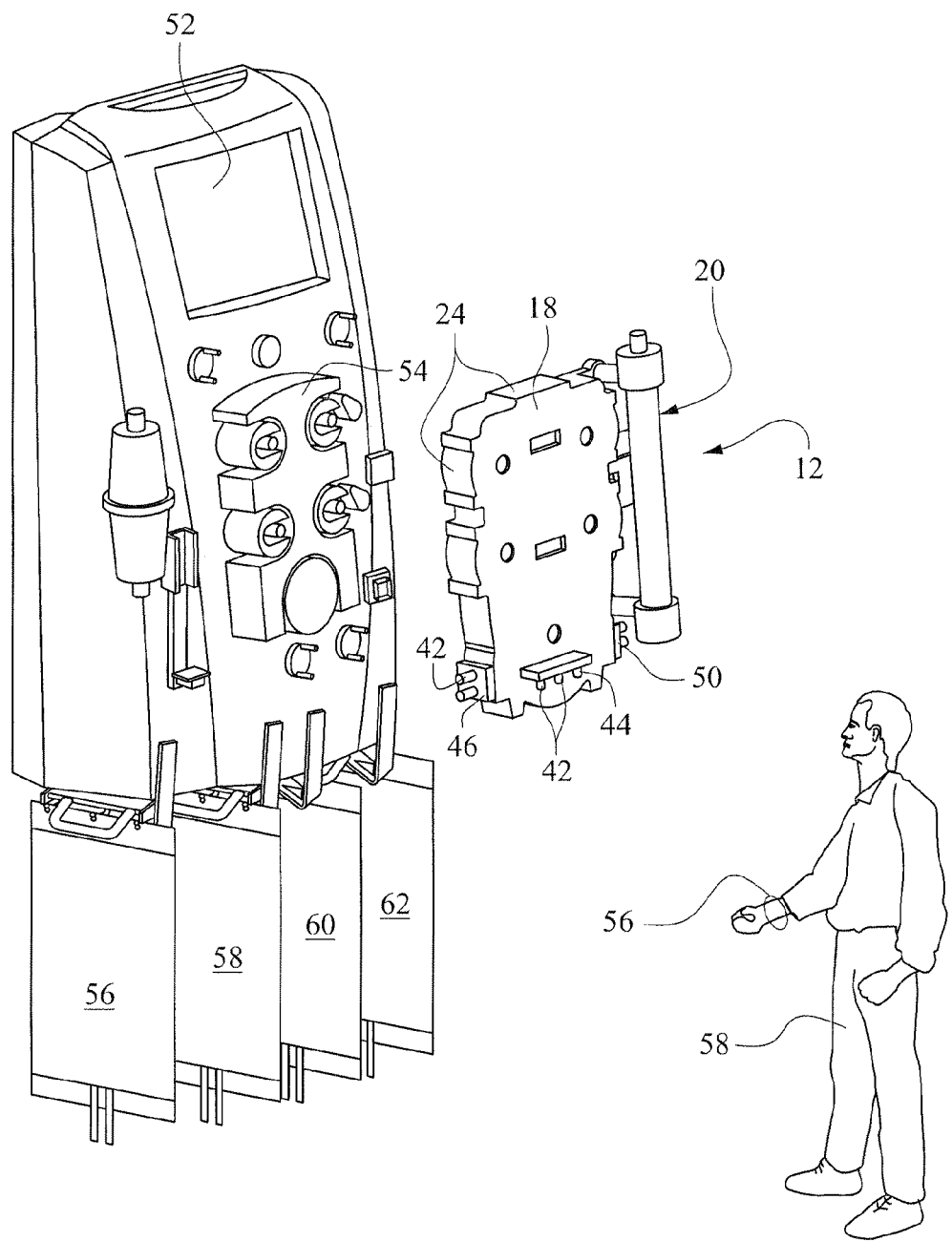
FIG. 2 is a schematic diagram of an extracorporeal cassette mounted to a blood treatment monitor wherein the lines from the cassette are not shown to avoid clutter in the illustration.

FIG. 2 shows an exemplary extracorporeal monitor 52 for a blood treatment system, such as a dialysis treatment system. The monitor generally includes pumps for blood, blood treatment liquids and filtrate liquids. A coupling 54 on the front of the monitor receives the cassette 22. The monitor, coupling 54 and arrangement of the cassette and hemodialyzer are exemplary and may vary. The brackets 46, 48 and 50 for the dummy luer lock connectors 42, 44 are shown as being attached to the cassette 18.

In operation, a medical professional, such as a nurse or medical technician, will remove the extracorporeal circuit 12 from its envelope and mount the cassette to the coupling 54 on the monitor. The free ends of the lines may remain attached to the dummy luer lock connectors until the cassette is attached to the monitor. Once the cassette is attached, the medical professional typically disconnects free ends of lines from the dummy luer lock connectors in a predetermined order. For example and as an alternative to the arrangement of brackets shown in FIG. 1, the lines associated with priming the extracorporeal circuit may be the first lines disconnected from the cassette. The lines associated with priming may be conveniently all connected to dummy luer lock connectors on the first mounting bracket 46. The lines for priming may be connected to a priming liquid container 56 and a container 58 for the effluent from the priming operation. In this alternative, the lines associated with blood access and blood treatment fluids are grouped on the second and third mounting brackets 48, 50.

After completion of priming, the medical professional may disconnect the lines connected to the dummy luer connectors on the second mounting bracket 48 and connect those lines to a blood access device 56 that provides withdrawal and infusion ports to the vascular system of a patient 58. In addition, the lines associated with blood treatment fluids and dialysate may be removed from the third mounting bracket 50 and attached to the container 60 holding the blood treatment fluid and the container 62 to receive the dialysate that is discharged from the blood treatment device 20. The lines, if any, used during priming and not used during the blood treatment may be reattached to the dummy luer lock connectors on the first mounting bracket before or during the blood treatment begins. Similarly, after blood treatment is completed and the extracorporeal circuit is ready to be removed from the monitor, the free ends of lines may be reattached to their respective dummy luer lock connectors. By reattaching unused lines, the dummy luer lock connectors can be used to stow lines after they have been used and prevent lines becoming tangled during or after the treatment. Reattaching the lines to the dummy luer lock connectors also reduces or prevents liquids from draining from the lines and onto a floor, and assists in gathering together the ends of the lines so that the used extracorporeal circuit may be placed back into the envelope for disposal.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. An extracorporeal circuit comprising:
   lines which include passages for blood or a medical liquid;
   a connector at a free end of each of the lines;
   a cassette supporting the lines; and
   dummy connectors attached to the cassette and each adapted to form a mating connection with a respective one of the connectors at the free ends of the lines, wherein a first group of the dummy connectors is attached to a sidewall of the cassette and a second group of the dummy connectors is attached to a front wall of the cassette, and
   wherein the connectors are arranged in accordance with a sequence in which the lines are attached for a blood treatment session or are grouped in accordance with types of liquids to flow through the lines during the blood treatment session.

2. The extracorporeal circuit of claim 1, wherein each group corresponds to a step of a sequence in which the lines are attached for a blood treatment session.

3. The extracorporeal circuit of claim 1, wherein each group corresponds to types of liquids to flow through the lines.

4. The extracorporeal circuit of claim 1, wherein the groups of dummy connectors are located on different zones of the cassette.

5. The extracorporeal circuit of claim 1, wherein the dummy connectors protrude from a first bracket and a second bracket each attached to the cassette, wherein the first bracket has dummy connectors to connect to the lines for blood, and the second bracket has dummy connectors to connect to the lines for a blood treatment liquid and a dialysate.

6. The extracorporeal circuit of claim 1, wherein the connectors and dummy connectors are each one of a male or female Luer lock connector.

7. The extracorporeal circuit of claim 1, wherein the first group of the dummy connectors protrudes in an orthogonal direction to a direction of protrusion of the second group of the dummy connectors.

8. The extracorporeal circuit of claim 1, wherein the dummy connectors include both male and female connectors.

9. The extracorporeal circuit of claim 1, wherein the dummy connectors include a third group, wherein one of the first, second and third groups of the dummy connectors is designated to stow the lines associated with moving a first blood treatment fluid into the circuit and discharging the first blood treatment fluid from the circuit, another of the first, second and third groups of the dummy connectors is designated to stow the lines associated with blood access to a vascular system of a patient, and a third of the first, second and third groups of the dummy connectors is designated to stow the lines associated with moving a dialysate into the circuit and discharging the dialysate from the circuit.

10. The extracorporeal circuit of claim 1, wherein the circuit is for dialysis and the circuit includes a hemodialyser.

11. The extracorporeal circuit of claim 1, wherein the cassette is configured to mount to an extracorporeal treatment monitor including pumps adapted to engage the lines to move liquids through the lines of the circuit.

12. The extracorporeal circuit of claim 1, comprising:
   a hydrophobic filter connected to at least one of the lines having one of the free ends capped with the connector, wherein the hydrophobic filter is permeable to gas and impermeable to liquids.

13. The extracorporeal circuit of claim 12, wherein the hydrophobic filter is a segment of said at least one of the lines.

14. The extracorporeal circuit of claim 12, wherein said at least one line having the free end capped with the connector includes at least one of the hydrophobic filters.

15. The extracorporeal circuit of claim 1, wherein first of the lines are associated with preparation of the extracorporeal circuit and are connected to first of the dummy connectors on a first side of the cassette, second of the lines are associated with blood and anti-coagulant and are connected to second of the dummy connectors on a second side of the cassette, and third of the lines are associated with blood treatment fluid and dialysate and are connected to third of the dummy connectors on a third side of the cassette.

16. The extracorporeal circuit of claim 1, comprising mounting brackets attached to the cassette, wherein the dummy connectors extend from the mounting brackets.

17. The extracorporeal circuit of claim 16, wherein the mounting brackets are releasably attached to the cassette.

18. The extracorporeal circuit of claim 16, wherein the mounting brackets are permanently attached to the cassette.

19. A method to stow free ends of lines in an extracorporeal circuit including a cassette and lines having passages for liquids, the method comprising:
   attaching a connector to cap a free end of one of the lines, wherein the connector includes a passage aligned with the passage of the capped line;
   assigning each of a plurality of dummy connectors to a respective one of the capped free ends of the lines;
   arranging the dummy connectors in groups and positioning the groups of dummy connectors on the cassette, wherein the groups correspond to a sequence in which the lines are to be attached for a blood treatment session or correspond to types of liquids to flow through the lines, wherein a first group of the dummy connectors is attached to a sidewall of the cassette and a second group of the dummy connectors is attached to a front wall of the cassette;
   stowing the free ends by coupling the connectors capping the free end of the lines to a respective one of the dummy connectors; and
   packaging the circuit with the stowed free ends of the lines in a package for shipment of the circuit.

20. The method of claim 19, wherein each group corresponds to a step of a sequence in which the lines are attached for a blood treatment session.

21. The method of claim 19, wherein each group corresponds to types of liquids to flow through the lines.

22. The method of claim 19, wherein the groups of dummy connectors are positioned on different zones of the cassette.

23. The method of claim 19, wherein the dummy connectors include a third group, wherein one of the first, second and third groups of the dummy connectors is designated to stow the lines associated with moving a first type of liquid into and out of the circuit, another of the first, second and third groups of the dummy connectors is designated to stow the lines associated with blood access to a vascular system of a patient, and a third of the first, second and third groups of the dummy connectors is designated to stow the lines associated with moving a second type of liquid into and out of the circuit.

24. The method of claim 19, further comprising: including a hydrophobic filter in at least one of the lines of the circuit and injecting a sterilization gas into the package through a hydrophobic membrane in the packaging such that the sterilization gas passes through the filter and enters said at least one line.

25. The package of claim 24, wherein the sterilization gas includes ethylene oxide.

26. The method of claim 19, wherein the extracorporeal circuit is for hemodialysis and the circuit includes a hemodialyser.

27. The method of claim 19, wherein the connectors and the dummy connectors are each one of a male or female Luer lock connector.

28. A package for an extracorporeal circuit, comprising:
an envelope;
an extracorporeal circuit comprising lines and a cassette supporting the lines;
a connector at a free end of each line; and
dummy connectors attached to the cassette and each coupled with a respective one of the connectors at the free ends of the lines,
wherein the dummy connectors are arranged in groups and positioned on the cassette,
wherein the groups correspond to a sequence in which the lines are to be attached for a blood treatment session or correspond to types of liquids to flow through the lines,
wherein the cassette comprises a front wall and sidewalls,
wherein a first group of the dummy connectors is attached to one of the walls of the cassette and a second group of the dummy connectors is attached to another wall of the cassette, and
wherein the extracorporeal circuit and the cassette are packaged in the envelope.

29. The package of claim 28, wherein lines associated with preparation of the extracorporeal circuit are connected to the dummy connectors on a first side of the cassette, lines associated with blood and anti-coagulant are connected to the dummy connectors on a second side of the cassette, and lines associated with blood treatment fluid and dialysate are connected to the dummy connectors on a third side of the cassette.

30. The package of claim 28, wherein the extracorporeal circuit is for hemodialysis and the circuit includes a hemodialyser.

31. The package of claim 28, comprising a hydrophobic filter connected to at least one of the lines.

32. The package of claim 31, wherein the envelope includes at least one hydrophobic filter panel.

33. The package of claim 32, wherein the envelope comprises opposing sheets sealed along a perimeter of the sheets and the hydrophobic filter panel is co-extensive with an opening in one of the sheets.

\* \* \* \* \*